US006281225B1

(12) United States Patent
Hearst et al.

(10) Patent No.: US 6,281,225 B1
(45) Date of Patent: Aug. 28, 2001

(54) INHIBITING PROLIFERATION OF ARTERIAL SMOOTH MUSCLE CELLS

(75) Inventors: John E. Hearst, Berkeley; William M. Greenman, San Francisco; Susan Wollowitz, Walnut Creek; Ryan D. Alfonso, Martinez, all of CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 09/330,314

(22) Filed: Jun. 10, 1999

Related U.S. Application Data

(60) Provisional application No. 60/089,008, filed on Jun. 11, 1998.

(51) Int. Cl.[7] .................................................. A61K 31/473

(52) U.S. Cl. .............................................................. 514/297

(58) Field of Search .............................................. 514/297

(56) References Cited

U.S. PATENT DOCUMENTS

| | | | |
|---|---|---|---|
| 4,824,436 | 4/1989 | Wolinsky | 604/53 |
| 5,116,864 | 5/1992 | March et al. | 514/455 |
| 5,171,217 | 12/1992 | March et al. | 604/53 |
| 5,279,565 | 1/1994 | Klein et al. | 604/105 |
| 5,354,774 | 10/1994 | Deckelbaum et al. | 514/455 |
| 5,559,250 | 9/1996 | Cook et al. | 549/282 |
| 5,599,844 | 2/1997 | Grainger et al. | 514/651 |
| 5,628,730 | 5/1997 | Shapland et al. | 604/21 |
| 5,733,925 | 3/1998 | Kunz et al. | 514/449 |
| 6,093,725 | 7/2000 | Cook et al. | 514/297 |

FOREIGN PATENT DOCUMENTS

| | | |
|---|---|---|
| WO 96/14737 | 5/1996 | (WO) . |
| WO 96/39818 | 12/1996 | (WO) . |
| WO 97/07674 | 3/1997 | (WO) . |
| 98/08566 * | 3/1998 | (WO) . |
| WO 98/30545 | 7/1998 | (WO) . |

OTHER PUBLICATIONS

Sirois et al. (1997). "Rat Arterial Wall Retains Myointimal Hyperplastic Potential Long After Arterial Injury," *Circulation* 96(4):1291–1298.

Yilmaz et al., Int. J. Cancer, 77(4), pp.592–599 (abstract), 1998.*

Barath et al. (Feb. 1989). "Low dose of antitumor agents prevents smooth muscle cell proliferation after endothelial injury" *JACC* 13(2):252A (Abstract).

Budowsky et al. (1996). "Principles of selective inactivation of the viral genome: Dependence of the rate of viral RNA modification on the number of protonizable groups in ethyleneimine oligomers" *Vaccine Res.* 5(1):29–39.

Cummings et al. (1991). "Determination of reactive nitrogen mustard anticancer drugs in plasma by high–performance liquid chromatography using derivatization" *Anal. Chem.* 63:1514–1519.

Fernández–Ortiz et al. (1994). "A new approach for local intravascular drug delivery" *Circulation* 89:1518–1522.

Fram et al. (1994). "Localized intramural drug delivery during balloon angioplasty using hydrogel–coated balloons and pressure–augmented diffusion" *JACC* 23(7):1570–1577.

Goldman et al. (1987). "Influence of pressure on permeability of normal and diseased muscular arteries to horseradish peroxidase: A new catheter approach" *Atherosclerosis* 65:215–225.

March et al. (1993). "8–methoxypsoralen and longwave ultraviolet irradiation are a novel antiproliferative combination for vascular smooth muscle" *Circulation* 87:184–191.

Moura et al. (1995). "Intramural delivery of agent via a novel drug–delivery sleeve: Histological and functional evaluation" *Circulation* 92:2229–2305.

Nabel et al. (Sep. 14, 1990). "Site–specific gene expression in vivo by direct gene transfer into the arterial wall" *Science* 249:1285–1288.

Nathan et al. (1995). "Local interventions for vasculoproliferative diseases" Chapter 2 in *Molecular Interventions and Local Drug Delivery*, Edelman et al. eds., W. B. Saunders Co.: London, pp. 29–52.

Riessen et al. (1993). "Arterial gene transfer using pure DNA applied directly to a hydrogel–coated angioplasty balloon" *Hum. Gene Ther.* 4:749–758.

Wolinsky et al. (1990). "Use of a perforated balloon catheter to deliver concentrated heparin into the wall of the normal canine artery" *JACC* 15(2):475–481.

* cited by examiner

*Primary Examiner*—Phyllis G. Spivack
(74) *Attorney, Agent, or Firm*—Morrison & Foerester LLP

(57) ABSTRACT

The present invention provides methods for inhibiting restenosis at a site of vascular recanalization. The methods include intravascular administration of a reactive acridine compound to the site of injury, without the requirement for activation or sustained release of the compound.

11 Claims, No Drawings

INHIBITING PROLIFERATION OF ARTERIAL SMOOTH MUSCLE CELLS

This application claims the benefit of Provisional No. 60/089,008 filed Jun. 11, 1998.

TECHNICAL FIELD

This invention relates to methods, compounds and devices for inhibiting smooth muscle proliferation at a site of injury.

BACKGROUND

Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerotic vessels has been coronary bypass surgery. More recently, however, vascular recanalization procedures for treating arteriosclerotic vessels have been developed. These procedures involve using intravascular devices threaded through blood vessels to the obstructed site, including for example, percutaneous transluminal angioplasty (PTA), also known as balloon angioplasty. Balloon angioplasty uses a catheter with a balloon tightly packed onto its tip. When the catheter reaches the obstruction, the balloon is inflated, and the atherosclerotic plaques are compressed against the vessel wall. A shortcoming of this and other intravascular procedures, however, is that in a number of individuals some of the treated vessels restenose (ie. the vessels narrow) by six months post-angioplastic treatment. The restenosis is thought to be due in part to mechanical injury to the walls of the blood vessels caused by the intravascular device.

The walls of most blood vessels are composed of three distinct layers, or tunics, surrounding a central tubular opening, the vessel lumen. The innermost layer that lines the vessel lumen is called the tunica intima. The middle layer, the tunica media, consists mostly of circularly arranged smooth muscle cells and connective tissue fibers. In a non-injured vessel the smooth muscle cells are normally not actively dividing. The outmost layer of the blood vessel wall, the tunica adventitia, is composed largely of collagen fibers that protect the blood vessel. Mechanical injury, resulting in damage to the tunica intima, initiates a number of events, including the release of chemicals such as platelet-derived growth factors (PDGF), which prompts the migration and proliferation of smooth muscle cells at the site of injury over many weeks.

Several methods for inhibiting smooth muscle cell proliferation following the use of an intravascular device have been reported. These include the administration of agents, including, for example, anti-proliferative agents such as cell cycle inhibitors and anti-coagulant agents, by local or systemic delivery systems. Delivery of agents systemically, however, has required dosages that are both prohibitively toxic and prohibitively costly. Local delivery of agents, for example heparin, as described in U.S. Pat. No. 4,824,436, has proven ineffective in inhibiting restenosis due in part to problems related to inadequate residence time at the site of injury before the agent diffuses to ineffective concentrations. Cell cycle inhibitors such as taxol, which do not react covalently and require prolonged residence time for effectiveness, are likely to have similar problems. In addition, prolonged residence times are likely to have a greater risk of toxicity.

Other methods reported for inhibiting smooth muscle cell proliferation involve locally delivering agents that are contained in sustained release formulations. In one example, agents contained within a physiologically compatible, biodegradable polymeric microparticle are delivered locally to the site of injury such that the agents are released from the arterial wall for 72 hours or more. U.S. Pat. No. 5,171,217. Still other methods reported for inhibiting smooth muscle cell proliferation involve administering photochemically activated agents by local delivery systems. In one example, photochemically activated agents, for example, 8-methoxypsoralen, are locally delivered to the site of injury and then activated by a visible light source. U.S. Pat. No. 5,354,774. Another approach is the use of radiation-emitting catheters or guide wires, which can cause damage to nucleic acid and inhibit smooth muscle cell proliferation. Each of these methods, however, requires an added level of complexity, namely incorporation of the agent on or within a sustained release formulation, photoactivation using a complex intravascular light source, or delivery of a radiation dose which requires the presence of a radiologist and presents exposure hazards to the attending personnel.

A need therefore exists for safer and less complex methods for inhibiting smooth muscle cell proliferation at a site of injury following vascular recanalization procedures.

SUMMARY OF THE INVENTION

The present invention includes methods for inhibiting smooth muscle cell proliferation in a blood vessel subjected to recanalization. The methods include administration of an alkylating compound, not in a sustained or controlled release process, to an individual undergoing vascular recanalization, by local delivery to the vascular recanalization site.

Advantages of the present invention include the following. First, because the compounds for use in the methods of the invention are rapidly taken up by cells, and they react rapidly and permanently with cellular nucleic acid, these compounds need not remain long at the site of administration to be effective. Unlike sustained exposure processes, the compounds and methods of the present invention have a sustained effect with a very short exposure time. Thus, the problem of insufficient residence time associated with local delivery of previously reported agents for inhibiting smooth muscle cell proliferation is overcome. In addition, because the compounds for use in the methods of the invention are rapidly taken up by cells, and they react rapidly with cellular nucleic acids, their toxicity can be significantly reduced by shorter exposure times and lower concentrations.

Second, administration of the alkylating compounds by local delivery to the site of the recanalization allows for the use of lower dosages as compared, for example, to the administration of these compounds by systemic delivery. Using lower dosages decreases the toxicity of these compounds A third advantage of the present invention is that the methods do not necessarily require the use of alkylating compounds in a sustained release formulation. Methods that do not require the incorporation of the compound on or within a sustained release formulation are easier to prepare and require less complex technology. While it is not required that the compounds of the present invention be used in a sustained release formulation, they would provide an advantage in such a formulation over current compounds for the reasons discussed above, i.e. they react rapidly and permanently such that lower concentrations and exposures are effective, which reduces the risk of toxicity and eliminates problems of formulating sufficiently high levels, in a sustained release formulation, for effectiveness.

A fourth advantage of the present invention is that the methods do not require use of an intravascular light source to activate the compounds for use in the methods of the invention, nor do they require irradiation. The lack of requirement for a source of light or radiation again allows for easier and less complex technology.

The methods of the invention use alkylating compounds which are rapidly taken up by cells and react rapidly with the intracellular nucleic acid to inhibit proliferation. In a preferred embodiment, an alkylating compound rapidly forms covalent bonds with the nucleic acid of a smooth muscle cell. Diffusion of the compound into a smooth muscle cell and reaction with smooth muscle cell nucleic acid sufficient to inhibit restenosis is essentially complete within 2 minutes, more preferably within one minute, and most preferably within 30 seconds after delivery of the compound to a site of vascular injury.

The alkylating compounds for use in the methods of the invention include those containing at least one chemically reactive moiety, referred to as an effector group, capable of reacting to form a covalent bond with a nucleic acid. Preferred effector groups include mustard, mustard intermediates and mustard equivalents. A particularly preferred class of mustards are aliphatic mustards.

The alkylating compounds for use in the methods of the invention may also be provided in a form that includes an effector group covalently bonded to a nucleic acid binding ligand, also referred to as an anchor group. Anchor groups may include, for example, intercalators, such as acridines and acridine derivatives. A preferred compound for use in the methods of the invention is quinacrine mustard.

In addition, the alkylating compounds for use in the methods of the invention may be provided in a form that includes an anchor group covalently bonded to a frangible linker, which is covalently bonded to the effector group. A preferred compound for use in the methods of the invention in this class is β-alanine, N-(acridin-9-yl), 2-[bis(2-chloroethyl)amino] ethyl ester.

The methods of the invention include administering the compounds for use in the invention by local delivery. In one embodiment, the compounds for use in the methods of the invention may be locally delivered by a catheter system. In a preferred embodiment, the compounds for use in the methods of the invention may be locally delivered by an infusion sleeve catheter. The compounds for use in the methods of the invention may be administered before, during or after the recanalization procedure.

In addition, the method may also involve the administration of a quencher. In one embodiment the quencher is a thiol type quencher, including for example, glutathione or thiol sulfate. Although there are naturally occurring quenchers that already exist in certain biological fluids, glutathione in the blood for example, it may be desirable in certain circumstances to increase their concentration or to administer other quenching agents. The quencher may be added by local or systemic delivery. If the quencher is administered systemically, the quencher may be added prior to, in proximal time with, or after the administration of the alkylating compounds for use in the methods of the invention. If the quencher is administered by local delivery, the quencher may be added in proximal time with or after the administration of the alkylating compounds for use in the methods of the invention.

MODES FOR CARRYING OUT THE INVENTION

Incorporation by Reference

References cited within this application, including patents, published patent applications and other publications, are hereby incorporated by reference.

Description of Preferred Embodiment

Treating arteriosclerosis with intravascular devices, including for example, ablative procedures or balloon catheters, is becoming increasingly popular as technology related to intravascular devices continues to improve. Approximately 1 million balloon angioplasty procedures alone are performed on an annual basis globally. These procedures, however, have a major shortcoming. In a significant number of cases the treated vessels re-occlude, or restenose, by six months post-treatment which requires the individual to undergo additional treatment. "Restenosis" refers to the stage at which the vessel lumen has decreased in diameter by about 50% or more as compared to the diameter of the vessel lumnen immediately following a vascular recanalization procedure.

The pathogenesis of restenosis is not well understood. It is believed to be due, in part, to recoil of the wall of the treated vessel. Additionally, it is hypothesized that vascular recanalization procedures used to treat diseases, such as arteriosclerosis, can cause mechanical injury at the site of recanalization. Without intending to be limited to any particular mechanism of action it is hypothesized that once intimal rupture occurs in the blood vessel a number of events begin to take place including the migration of monocytes to the subendothelial layer of the intima and the release of mitogenic growth factors, including, for example, platelet-derived growth factor (PDGF), macrophage-derived growth factor (MDGF), and endothelial cell-derived growth factor (EDGF). These chemicals, and in particular PDGF, apparently play a role in inducing smooth muscle cell proliferation which in turn produces substantial quantities of intercellular substances which build up, and the intima begins to thicken. Methods for measuring the proliferating ability of smooth muscle cells are known to those of skill in the art, including for example, assays that measure the uptake of [$^3$H]-thymidine by smooth muscle cells, as described in March et al., *Circulation*, 87:184–191 (1993), and immunoassays for detecting human cytokines, including for example, interleukin 1β (IL-1β), interleukin 8, vascular endothelial growth factor (VEGF), platelet-derived growth factor (PDGF) and endothelin-1.

The methods of the present invention are directed at inhibiting restenosis caused, for example, by intimal thickening occurring after vascular recanalization procedures. "Vascular recanalization" refers to a procedure for restructuring a vessel, including, for example, ablative and angioplastic procedures. "Inhibiting restenosis" refers to substantially inhibiting smooth muscle cell proliferation in a statistically significant fashion; for example, inhibiting smooth muscle cell proliferation by about 50%, or preferably by about 80%, and more preferably by about 95% as compared to an untreated control. It is not essential, however, that the methods of the present invention result in the inhibition of all proliferating smooth muscle cells. It is sufficient that smooth muscle cell proliferation is arrested at the site of treatment such that the remaining fraction of proliferating smooth muscle cells is insufficient to cause restenosis. "Inhibiting restenosis" also refers to reduction in intimal thickening and reduction in the narrowing of luminal diameter.

Modes of Administration

The methods of the present invention include administering compounds for use in the invention by local delivery systems. The compounds for use in the present invention may be administered by local delivery at a time proximal to the recanalization procedure or at a time after the recanalization procedure. The delivery time of the compounds for use in the present invention is less than about 3 minutes, more preferably less than about 60 seconds, and most preferably less than about 30 seconds from the time of initial administration. The compounds for use in the invention may be delivered in a single dose or delivered in repeat doses.

Non-limiting examples of local delivery systems for use in the present invention include intravascular drug delivery catheters, wires, pharmacological stents and endoluminal paving.

In a preferred embodiment the compounds for use in the present invention are administered to the site of recanalization by direct intravascular deposition using intravascular catheters. Catheter systems for use in the present invention, include, for example, pressure-driven catheters, diffusion catheters and mechanical catheters. See, e.g. Wolinsky & Thung, *J. Am. Coll. Cardiol.*, 15:475–81 (1990); Goldman et al., *Atherosclerosis*, 65:215–25 (1987); Nabel et al., *Science*, 294, 1285–8 (1990); Fram et al., *J Am. Coll. Cardiol.*, 23:1570–71 (1994); Riessen et al., *Human Gene Ther.*, 4, 749–58 (1993); Fernandez-Ortiz et al., *Circulation*, 89:1518–22 (1994).

In one embodiment, the administration of compounds for use in the methods of the present invention may be by pressure-driven catheter systems, including for example, porous catheters; microporous catheters, for example, those made by Cordis Corporation; macroporous catheters; transport catheters, for example, those made by Cardiovascular Dynamics/Boston Scientific; channeled balloon catheters, for example, those made by Boston Scientific; and infusion sleeve catheters, for example, those made by LocalMed.

In a preferred embodiment the methods of the invention utilize a pressuredriven based catheter that is an infusion sleeve catheter, an example of which is described by Moura et al, *Circulation*, 92: 2229–2305 (1995) and further described in U.S. Pat. No. 5,279,565, hereby incorporated by reference.

The infusion sleeve, an example of which is that produced by LocalMed, is designed to allow independent control of both the apposition of drug-delivery systems against the arterial wall and the drug delivery of the agent into the wall. The efficacy of drug delivery by an infusion sleeve on the arterial architecture of a vessel is a function of proximal delivery pressure. In one embodiment, the effect of proximal pressure on delivery of compounds used in the methods of the present invention by an infusion sleeve catheter can be determined in vitro by histological evaluation of the treated artery by known methods. In one non-limiting example, a proximal pressure of between about 50 to 200 psi may be used to deliver, by an infusion sleeve catheter, the compounds for use in the methods of the present invention, preferably, between about 100 to about 150 psi, and most preferably, between about 50 to 100 psi.

In another embodiment, the compounds of the invention may be administered locally by diffusion-based catheter systems, including for example, double balloon, dispatch, hydrogel and coated stent catheters. The methods of the invention also include local administration of the compounds used in the methods of the present invention by mechanical device-based catheter systems, including for example, iontophoretic balloon catheters.

The ability to locally deliver the compounds used in the present invention may be evaluated in vivo using known animal models, including for example, acute canine coronary models. For example, a compound for use in the methods of the present invention is administered by local delivery to a canine at a site of injury. The canine is sacrificed and then examined by known methods, including, for example, fluorescence microscopy.

Optimum conditions for delivery of the compounds for use in the methods of the invention may vary with the different local delivery systems used, as well as the properties and concentrations of the compounds used. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Conditions which may be optimized include, for example, the concentrations of the compounds, the delivery volume, the delivery rate, the depth of penetration of the vessel wall, the proximal inflation pressure, the amount and size of perforations and the fit of the drug delivery catheter balloon.

Compounds For Use In The Methods Of The Invention

The methods of the present invention include the administration, by local delivery to a site of injury, of compounds that have the ability to bind to and react rapidly with the nucleic acids of smooth muscle cells to block cellular replication. The exposure time of the compounds at the site of injury may be for a short period of time while still producing the desired inhibition of restenosis. Without intending to be limited to any particular mechanism of action it is hypothesized that the methods of the present invention are able to inhibit smooth muscle proliferation so as to reduce or inhibit restenosis by using compounds that have fast kinetics of activation such that they are able to react rapidly with the nucleic acid of the smooth muscle cells to retard replication before the compounds diffuse to concentrations that are ineffective for inhibition of restenosis.

The compounds for use in the methods of the present invention include at least one chemically reactive moiety, referred to as an "effector group", capable of reacting to form a covalent bond with a nucleic acid. In one embodiment, the effector moiety is selected from the group consisting of a mustard, mustard intermediate and a mustard equivalent.

A "mustard group" is defined herein as including mono or bis haloethylamine groups, and monohaloethylsulfide groups. A particularly preferred class of mustards are aliphatic mustards. For example, nitrogen mustard, $CH_3—N(CH_2CH_2Cl)_2$, is one of the simplest compounds containing a mustard group.

The methods of the invention also include the use of "mustard intermediates". Mustards can form reactive intermediates such as aziridinium or aziridine complexes and sulfur analogs of these complexes. In one embodiment, the effector can be a mustard intermediate, for example an aziridine covalently attached to a polyamine anchor may be used, as described in Budowsky et al., *Vaccine Research* 5:29–39 (1996); and PCT WO 97/07674, the disclosures of which are incorporated herein by reference.

The methods of the invention also include compounds containing functional groups that are the "equivalent of mustards." Mustard group equivalents are defined as those in which the halide of the mustard is replaced with a different leaving group, such as mono or bis mesylethylamine groups, mono mesylethylsulfide groups, mono or bis tosylethylamine groups, and mono tosylethylsulfide groups; and/or those which react by a mechanism similar to that by which mustards react, such as an epoxide.

The methods of the present invention also comprise the administration by local delivery to the site of injury of compounds that include an effector group covalently bonded to a nucleic acid binding ligand.

A "nucleic acid binding ligand", (or "anchor") is herein defined as a group which has an affinity for and can bind to nucleic acids non-covalently. While not limited to any particular mechanism, it is believed that the nucleic acid binding ligand functions as a carrier (or anchor) that targets (or directs) the molecule to nucleic acids, interacting non-covalently therewith. The anchor-effector arrangement enables the compounds to bind specifically to nucleic acid (due to the anchor's binding ability). This brings the effector into proximity for reaction with the nucleic acid. There are several modes of binding to nucleic acids. Compounds which bind by any of the following modes, combinations of them, or other modes are considered nucleic acid binding ligands. While the invention is not limited to the following compounds for use in the methods of the present invention, some examples of nucleic acid binding ligands are:

a) intercalators, such as, acridines (and acridine derivatives, e.g. proflavine, acriflavine, diacridines, acridones, benzacridines, quinacrines), actinomycins, anthracyclinones, rhodomycins, daunomycin, thioxanthenones (and thioxanthenone derivatives, e.g. miracil D), anthramycin, mitomycins, echinomycin (quinomycin A), triostins, ellipticine (and dimers, trimers and analogs thereof), norphilin A, fluorenes (and derivatives, e.g. flourenones, fluorenodiamines), phenazines, phenanthridines, phenothiazines (e.g., chliorpromazine), phenoxazines, benzothiazoles, xanthenes and thioxanthenes, anthraquinones, anthrapyrazoles, benzothiopyranoindoles, 3,4-benzopyrene, 1-pyrenyloxirane, benzanthracenes, benzodipyrones, quinolines (e.g., chloroquine, quinine, phenylquinoline carboxamides), furocoumarins (e.g., psoralens and isopsoralens), ethidium, propidium, coralyne, and polycyclic aromatic hydrocarbons and their oxirane derivatives;

b) minor groove binders such as distamnycin, netropsin, other lexitropsins, Hoechst 33258 and other Hoechst dyes, DAPI (4',6-diamidino-2-phenylindole), berenil, and triarylmethane dyes;

c) major groove binders such as aflatoxins;

d) molecules that bind by electrostatics (phosphate backbone binders), such as spermine, spermidine, and other polyamines; and e) nucleic acids or analogs which bind by sequence specific interactions such as triple helix formation, D-loop formation, and direct base pairing to single stranded targets. Derivatives of these compounds are also non-limiting examples of anchor groups, where a derivative of a compound includes, but is not limited to, a compound which bears one or more substituents of any type at any location, oxidation or reduction products of the compound, etc.

An exemplary compound for use in the methods of the present invention, is quinacrine mustard, the structure of which is shown below.

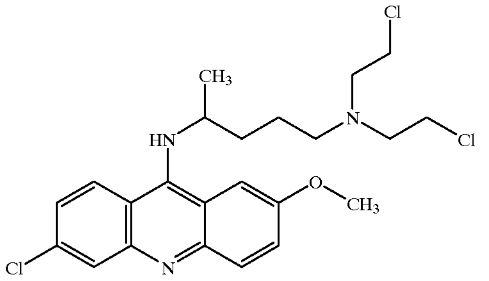

Other examples of compounds for use in the methods of the present invention which include an effector group and an anchor are disclosed in PCT WO 96/14737, PCT WO 96/39818, and U.S. Pat. No. 5,559,250, the disclosures of which are incorporated by reference herein.

The methods of the present invention further comprise the administration by local delivery to the site of injury of compounds that include an anchor group covalently bonded to a frangible linker, which is covalently bonded to an effector group, referred to herein as a FRALE.

The term "frangible linker" refers to a moiety which serves to covalently link the anchor and effector, and which will degrade under certain conditions so that the anchor and effector are no longer linked covalently. Like the alkylating compounds described above, the anchor-frangible linker-effector arrangement enables the compounds to bind specifically to nucleic acid. This brings the effector into proximity for reaction with the nucleic acids. Compounds including an anchor-frangible linker-effector arrangement are disclosed in PCT publication WO 98/30545, for which the corresponding U.S. application has issued as U.S. Pat. No. 6,093,725, the disclosure of which is incorporated herein by reference.

Examples of frangible linkers for use in the methods of the present invention, include, but are not limited to, moieties that include functional groups such as ester (where the carbonyl carbon of the ester is between the anchor and the $sp^3$ oxygen of the ester; this arrangement is also called "forward ester"), "reverse ester" (where the $sp^3$ oxygen of the ester is between the anchor and the carbonyl carbon of the ester), thioester (where the carbonyl carbon of the thioester is between the anchor and the sulfur of the thioester, also called "forward thioester"), reverse thioester (where the sulfur of the thioester is between the anchor and the carbonyl carbon of the thioester, also called "reverse thioester"), forward and reverse thionoester, forward and reverse dithioic acid, sulfate, forward and reverse sulfonates, phosphate, and forward and reverse phosphonate groups. "Thioestef" designates the —C(=O)—S— group; "thionoester" designates the —C(═S)—O— group, and "dithioic acid" designates the —C(═S)—S— group. The frangible linker also may include an amide, where the carbonyl carbon of the amide is between the anchor and the nitrogen of the amide (also called a "forward amide"), or where the nitrogen of the amide is between the anchor and the carbonyl carbon of the amide (also called a "reverse amide"). For groups which can be designated as "forward" and "reverse", the forward orientation is that orientation of the functional groups wherein, after hydrolysis of the functional group, the resulting acidic function is covalently linked to the anchor moiety and the resulting alcohol, thiol or amine function is covalently linked to the effector moiety. The reverse orientation is that orientation of the finctional groups wherein, after hydrolysis of the functional group, the resulting acidic function is covalently linked to the efector moiety and the regulting alcohol or thiol function is covalently linked to the anchor moiety.

Exemplary compounds for use in the methods of the present invention include β-alanine, N-(acridin-9-yl), 2-[bis(2-chloroethyl)amino]ethyl ester and β-alanine, N-(acridin-9-yl), 2-[bis(2-chloroethyl)amino]ethyl amide, the structures of which are shown below. These compounds were synthesized as described in PCT publication WO 98/30545, the disclosure of which is incorporated by reference herein. β-alanine, N-(acridin-9-yl), 2-[bis(2-chloroethyl)aniino] ethyl ester includes a frangible linker with an ester finctionality, while β-alanine, N-(acridin-9-yl), 2-[bis(2-chloroethyl)amino]ethyl amide includes a frangible linker with an amide functionality.

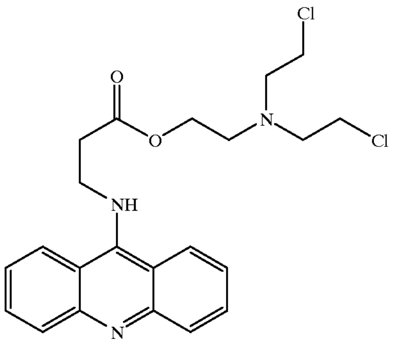

β-alanine, N-(acridin-9-yl),
2-[bis(2-chloroethyl)amino]ethyl ester

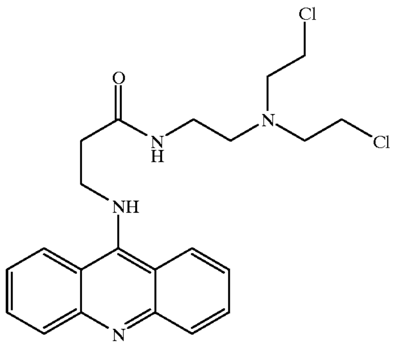

β-alanine, N-(acridin-9-yl),
2-[bis(2-chloroethyl)amino]ethyl amide

Additional compounds for use in the methods of the present invention are given below and include all salts thereof.

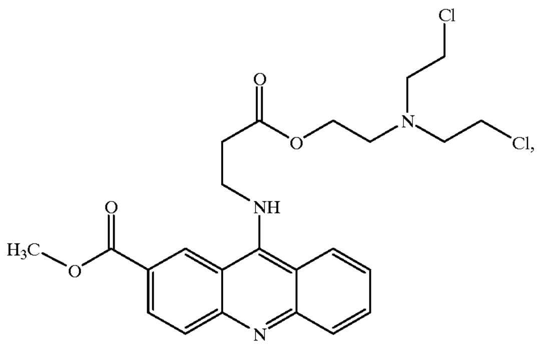

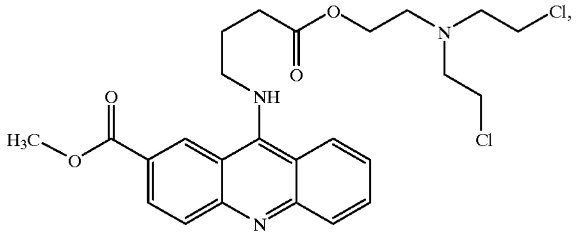

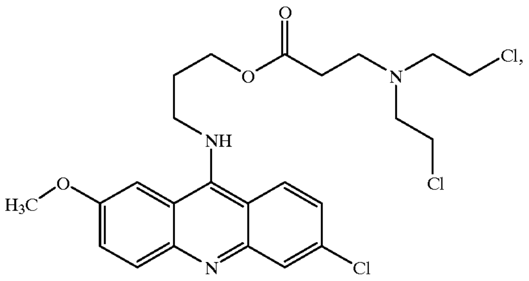

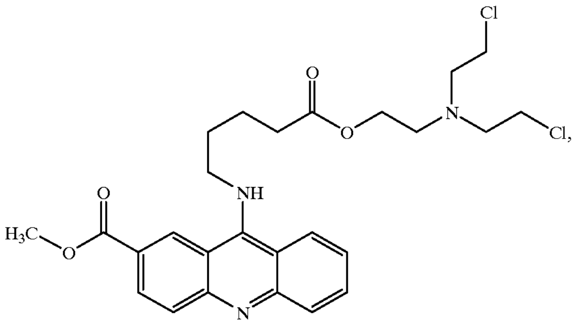

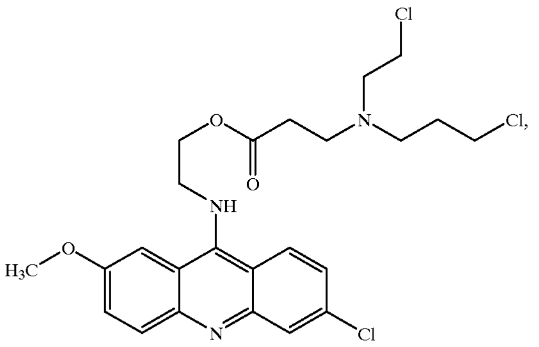

-continued

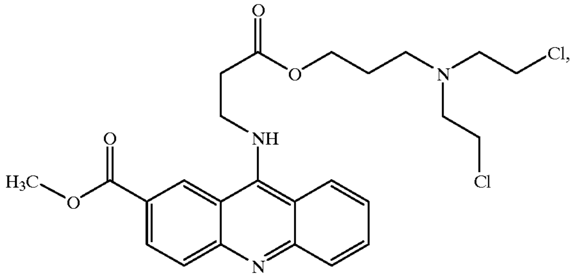

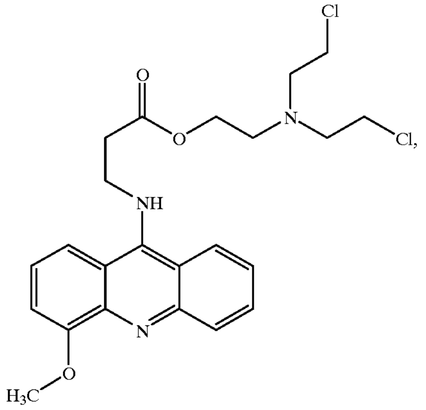

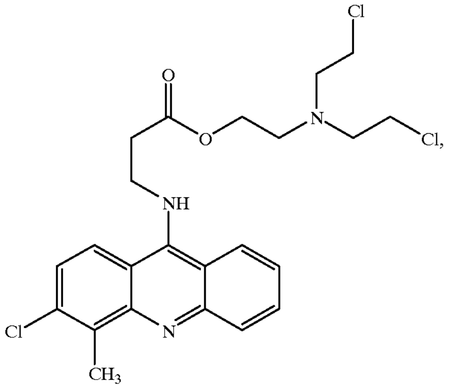

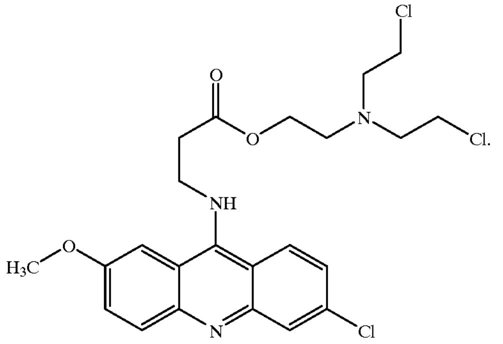

The reactivity of the compounds for use in the methods of the present invention may be enhanced by making modification on the effector moiety, or in the case of the FRALE compounds, on either the effector or linker moieties. Modifications on the effector moiety may change the compounds reactivity towards alkylation, while modifications on the substituents of the linker group may change the reactivity toward hydrolysis of this group. An enhancement of the alkylation reaction results in a faster formation of DNA adducts which is thought to correlate with cellular inactivation. An enhancement of the hydrolysis reaction is thought to result in a faster decomposition of the compound to less toxic and less mutagenic endproducts. Conditions which may be optimized for enhancing the reactivity of the compounds for use in the methods of the present invention include the equilibration rate of the compound intra- and extracellularly, the rate of reaction with the nucleic acid of the cells and the rate of the ester hydrolysis. In one embodiment, the compounds for use in the present invention have a fast and favorable equilibration towards the intracellular space, complemented by a reactive effector group with a comparable reaction rate. In another embodiment, the hydrolysis rate of the linker, although fast, is slightly slower than the alkylation rate of the compound. In one nonlimiting example, the hydrolysis rate of the linker is between about 2 to 10 times slower than the alkylation rate of the effector moiety of the compounds for use in the invention.

The alkylator reactivity of the compounds for use in the methods of the present invention may be enhanced by the replacement of the leaving groups (for example the chloride ions of the two compounds descibed above) with better leaving groups, which will allow for the faster formation of the reactive intermediate aziridinium ion, including for example, bromide or methansulfonate or other groups which are the conjugate bases of strong acids. The alkylator reactivity of the compounds for use in the methods of the present invention may also be enhanced by substituting the nitrogen heteroatom with another heteroatom of appropriate reactivity, such as phosphorous or arsenic. Enhancement of the reactivity of the FRALE may also be achieved by the enhancement of the nucleophilicity of the alkylator nitrogen. This may be achieved by the appropriate substitutions of the hydrogen atoms on, for example, the chloroethyl groups of the effector.

The reactivity toward hydrolysis of the linker group is dependent in part on two factors, including: 1) the length of the alkyl group which connects the ester group to the anchor moiety, and 2) the length of the allyl group which connects the ester group to the amine atom of the effector moiety. In both instances the hydrolysis rates increase as the length of the two chains decrease. This obscrytion holds true for both the standard and the inverse ester arrangement.

The reactivity of the compounds used in the methods of the present invention can be affected by their formulation, and by physiological conditions at the site to which they are delivered, including, for example, pH and temperature.

Formulations

The methods of the invention include different formulations by which the compounds for use in the methods of the invention are delivered. The alkylating compounds for use in the present invention can, for example, be introduced as an aqueous solution in water, saline, a synthetic medium or a variety of other media. The alkylating compounds can be provided with or without adjuvants. In addition, subsequent to the administration of the alkylating compounds, a gel may be delivered to the treated site. The gel acts to coat the compounds so as to prevent the compounds from being washed away by the naturally occurring biological fluids for about 3 hours from the time of administration. Further, the alkylating compounds can be introduced alone, or in a "cocktail" or mixture of several different alkylating compounds.

In a non-limiting example, the compounds of the present invention can be administered at a concentration of between about 10 nM to about 100 $\mu$M, more preferably between about 100 nM to about 1 $\mu$M, and most preferably less than about 300 nM.

Evaluating the Effectiveness of Methods of the Present Invention in Inhibiting Smooth Muscle Cell Proliferation in a Blood Vessel Subjected to Recanalization The effectiveness of the methods of the present invention can be measured by methods that are known in the art, including for example, methods for measuring the inhibition of smooth muscle cell proliferation (e.g., measuring the uptake of [$^3$H]-thymidine by smooth muscle cells) or methods for measuring changes in arterial blockage.

For example, the effectiveness of the methods of the present invention can be measured by the uptake of [$^3$H]-thymidine by smooth muscle cells in vitro following treatment according to the methods of the present invention. The conditions used in the methods of the present invention are such that the uptake of [$^3$H]-thymidine by smooth muscle cells is reduced by about 50% as compared to an untreated control, preferably by about 80%, most preferably by about 95%.

In another example, the effectiveness of the methods of the present invention is measured in vitro by assaying for production of human cytokines that are connected with cell proliferation and response to injury, including for example, the production of interleukin 1 β (IL-1β), interleukin 8, vascular endothelial growth factor (VEGF), platelet-derived growth factor (PDGF) and endothelin-1. Cytokine levels may be measured with commercially available immunoassays, including ELISA, manufactured for example by Genzyme Diagnostics, Cambridge, Mass. or R&D Systems, Minn., Minn. The conditions used in the methods of the present invention are such that the production of cytokines is reduced by about 50%, preferably by about 80% and most preferably by about 95% as compared to an untreated control.

The effectiveness of the methods of the present invention can also be measured by treating proliferating cells in culture with the alkylating compounds of the invention, counting cell number over time using, for example, a hemacytometer, and comparing to cell number of control cultures which have not been so treated. The conditions used in the methods of the present invention are such that cell number increases over a period of up to 28 days by no more than about 100%, more preferably by no more than about 50%, still more preferably, by no more than about 20%, and most preferably by no more than about 5%.

In another example, the effectiveness of the methods of the present invention is measured in vitro by the content of nuclear DNA in smooth muscle cells in culture at specific time points after treatment with alkylating compounds used in the methods of the present invention. Nuclear DNA content is measured by standard flow cytometric methods known in the art. Protocols for such measurements are detailed in the literature. See, e.g. March et al., *Circulation* 87:184–191 (1993). After treatment, the nuclear DNA content of treated cells increases no more than about 50%, preferably, no more than about 10%, and most preferably, no more than about 5%, compared to control, untreated cells.

The ability to locally deliver the compounds used in the present invention, and the effectiveness of these compounds, are evaluated in vivo using known animal models, including for example, rodent, rabbit, pig, or canine coronary models. For example, a compound for use in the methods of the present invention or a radiolabelled equivalent is administered by local delivery to an animal at a site of intravascular injury. At appropriate time intervals (e.g. minutes for the assessment of delivery, appropriate intervals for cell proliferation to occur for assessing the effectiveness) the animal is examined e.g. for compound distribution, vessel lumen diameter, or intimal thickness by known methods, including, for example, fluorescent microscopy and ultrasound.

In one example, the effectiveness of the methods of the present invention is measured in vivo in an animal model by measurment of luminal diameter of a vessel. For example, luminal diameter is measured upon follow-up angiogram six months after initial treatment. The diameter of the lumen is measured, for example, by angiography, intravascular ultrasound imaging, or any other method known to those of skill in the art. Luminal diameter upon follow-up angiogram, for example, six months after initial treatment, decreases by no more than about 50%, more preferably by no more than about 10%, and most preferably by no more than about 5%, relative to the diameter immediately after treatment.

In another example, the effectiveness of the methods of the present invention are measured in vivo in animal models by the thickening of the intima, for example, upon follow-up six months after initial treatment. The thickness of the intima is measured by methods known to those of skill in the art, such as sectioning and histological analysis of treated vessels. The intimal thickness upon follow-up, for example, six months after initial treatment, increases no more than about 50%, more preferably no more than about 10%, and most preferably no more than about 5% relative to the thickness immediately after treatment.

In another example, the effectiveness of the methods of the present invention are evaluated in vitro by observation of human smooth muscle cell proliferation as a function of treatment dose and time of treatment. The smooth muscle cells can be cultured following treatment and observed under a microscope in order to asign a score which indicates whether the cells are proliferating and whether they are still viable cells. Based on the scoring scale of Example 1, a compound for use in the method of treatment is preferred in which the treated cells score +/−, 1+, or 2+, more preferably 1+. In a preferred embodiment, the compounds of the present invention at concentrations between about 100 nM and 10 μM exhibit these scores, more preferably between about 100 nM and 1 μM with exposure times between about 15 seconds and 3 minutes, preferably with exposure times of less than 1 minute, more preferably less than 30 seconds. In another preferred embodiment, the compounds of the present invention at concentrations between about 100 nM and 1 μM exhibit a score of 1+with exposure times of less than 30 seconds.

Quenching

The methods of the present invention can also include a quenching step. "Quenching" refers to a method for reducing unwanted side reactions of a reactive alkylating compound and/or any of its chemical products. For example, in one embodiment, the compounds for use in the methods of the invention-are administered to an individual at a site of injury by local delivery. Once the compounds have had sufficient exposure time to the site of injury to cause the desired inhibition of smooth muscle cell proliferation a quenching step can be added.

Naturally occurring quenchers including, for example, glutathione, already exist in certain biological fluids including, for example, blood. Therefore, in some situations, for example when the biological fluid is blood and the naturally occurring glutathione is present in an amount effective to reduce unwanted side reactions of a reactive alkylating compound and/or any of its chemical products to the desired level, a quenching step may not be necessary. However, in other situations, for example when the concentration of the naturally occurring quencher is present in an amount insufficient to reduce the unwanted side reactions of a reactive alkylating compound and/or any of its chemical products, it may be desirable to add an additional amount of quencher to increase the reduction in unwanted side reactions to the desired level. In one embodiment, mixtures of different quenching compounds, either naturally occurring or non-naturally occurring, may be used.

Quenching compounds for use in the present invention can comprise, for example, a nucleophilic functional group that is capable of covalently reacting with an electrophilic group on the alkylating compound. Excmpluy nucleophilic groups include thiol, thioacid, dithioic acid, thiocarbamate, dithiocarbamate, amine, phosphate, and thiophosphate groups. The quencher may be, or contain, a nitrogen heterocycle such as pyridine. The quencher can be a phosphate containing compound such as glucose-6-phosphate. The quencher also can be a thiol containing compound, including, but not limited to, glutathione, cysteine, N-acetylcysteine, mercaptoethanol, dimercaprol, mercaptan, mercaptoethanesulfonic acid and salts thereof, e.g., MESNA, homocysteine, aminoethane thiol, dimethylaminoethane thiol, dithiothreitol, and other thiol containing compounds. One preferred quencher is glutathione. Other thiol containing compounds include methyl thioglycolate, thiolactic acid, thiophenol, 2-mercaptopyridine, 3-mercapto-2-butanol, 2-mercaptobenzothiazole, thiosalicylic acid and thioctic acid. Exemplary aromatic thiol compounds include 2-mercaptobenzimidazolesulfonic acid, 2-mercaptonicotinic acid, napthalenethiol, quinoline thiol, 4-nitrothiophenol, and thiophenol. The quencher also can be a peptide compound containing a nucleophilic group. For example, the quencher may be a cysteine containing compound, for example, a dipeptide, such as GlyCys, or a tripeptide, such as glutathione.

The quenchers can be administered to the individual by systemic or local delivery. If the quencher is administered to the individual systemically, the quencher can be added, for example, prior to, in proximal time with, or after the administration of the compounds for use in the methods of the invention. If the quencher is administered by local delivery, the quencher may be added, for example, in proximal time with, or after the administration of the compounds for use in the methods of the invention. In either situation it is important that the compounds for use in the methods of the invention have had sufficient exposure time with the site of injury to cause the desired inhibition of smooth muscle cell proliferation before the quenching effect takes place.

For use in the methods of the present invention quenchers are preferred which substantially decrease the concentration of reactive electrophilic alkylating species after uptake at the site of injury has occurred. The presence and concentration of a reactive electrophilic species is determined using methods known in the art. Cummings etal. (1991) *Anal. Chem.* 63:1514.

The concentration of the alkylating compound and the quenching agent are adjusted as needed to produce the desired reduction ofunwanted side reactions, while still producing the desired inhibition of restenosis.

The following examples are intended to illustrate the invention described herein but not to limit its scope. Certain modifications to the methods will be readily apparent to one of skill in the art.

EXAMPLES

Example 1

Inhibition of cultured Human Aortic Smooth Muscle Cells and Vero cells with β-alanine, N-(acridin-9-yl), 2-[bis(2-chloroethyl)amino]ethyl ester This example demonstrates that 0-alanine, N-(acridin-9-yl), 2-[bis(2-chloroethyl)amino]ethyl ester inhibits the increase in the number of cultured Human Aortic Smooth Musele Cells and Vero cells in a dose-dependent manner.

The first experiment was done on Vero cells (a monkey kidney cell line). The second experiment was done with T/G HA-VSMC cells (a human aortic smooth muscle cell system).

Vero cells:

Vero cells at passage 130 were seeded into the wells of three 6-well tissue culture plates (Corning, Corning N.Y.) at a volumetric split density of 1:10 in 3.0 mLs/well Eagles' and Earle's Modified Essential Medium (Life Technologies, Inc., Grand Island, N.Y.) with antibiotics and 10% Fetal Bovine Serum (FBS; Intergen Co., Purchase N.Y.). The plates containing Vero cells were incubated for approximately 48 hours to allow the attachment and growth of the cells to between 50 and 70% confluence. No effort was made to synchronize the growth phase of the Vero cells.

Three-fold seral dilutions of a stock solution of β-alanine, N-(acridin-9-yl), 2-[bis(2-chloroethyl)amino]ethyl ester were made in unbuffered saline solution (BBS, blood bank saline) to generate concentrations from 3 mM to 23 pM. Dilutions were made immediately prior to use to avoid the possibility of compound degradation.

The growth medium was removed from the Vero cell-containing plates. The cell monolayer was then washed several times with between 2 and 5 mL of BBS to remove all medium constituents which may quench the activity of β-alanine, N-(acridin-9-yl), 2-[bis(2-chloroethyl)amino] ethyl ester. The BBS was removed from all wells and 100 μL of each dilution of β-alanine, N-(acridin-9-yl), 2-[bis(2-chloroethyl)amino]ethyl ester, prepared as described above, was added to 1 well each of the 6-well plates. The plates were gently rocked back and forth for the 3 minute exposure period to ensure uniform distribution of the P-alanine, N-(acridin-9-yl), 2-[bis(2-chloroethyl)amino]ethyl ester and to guarantee that the monolayer did not dry due to exposure to air.

At the conclusion of the three minute incubation, between 4 and 6 mL of Phosphate Buffered Saline at pH 7.2 (PBg; Life Technologies) was added to each well and immediately removed by aspiration, followed by subsequent washing with PBS to ensure complete removal of the β-alanine, N-(acridin-9-yl), 2-[bis(2-chloroethyl)amino]ethyl ester. This was followed by the addition of growth medium which contained 0.75% molten Seaplaque® Agarose (FMC, Rockland Me.) to ensure that killed cells remained in close association with the monolayer and could be scored. Without the addition of the agarose overlay, dead cells detach from the plastic substrate, float off and are unavailable for evaluation. The medium also contained 10% FBS for growth promotion, to permit proliferation of cells insufficiently affected by the treatment. The plates were then briefly allowed to cool at approximately 22° C. to allow the agarose to harden. Treated cells were then incubated in a 37° C. humidified 5% $CO_2$ incubator (Forma Scientific, Marietta Ohio.).

Growth of the cell monolayers was scored when a differential growth rate could be determined, in this case three days following treatment. Twenty-four hours prior to being scored, 3 mL of growth medium containing Neutral Red dye was added to each well. The presence of the dye facilitates the ability to score the monolayer with the naked eye and with the use of a Stereo-zoom microscope (Zeiss, Germany). Growth was scored subjectively by the careful evaluation of each treated culture. Scores were assigned to each culture according to the scale defined in the results section, infra.

T/G HA-VSMC:

T/G Human Aortic Smooth Muscle Cells (obtained from the ATCC, American Type Culture Collection) were used at passage 19 in this study. The culture medium was F-12K medium with ITS-A reagent(insulin, transferrin and selenium supplement for adherent cell lines), TES and HEPES buffers, ECGS (endothelial cell growth supplement), freshly prepared ascorbate, glutamine, penicillin-streptomycin, and 10% FBS (Intergen) (all other reagents, Life Technologies).

β-alanine, N-(acridin-9-yl), 2-[bis(2-chloroethyl)amino] ethyl ester treatment conditions were similar to those described in the Vero cell experiment, supra, with the following exceptions: T/G HA-VSMC's were treated after 24 hours of adherence and growth in the 6-well plates, and growth was scored 6 days following treatment.

Results:

Growth Scoring of β-alanine, N-(acridin-9-yl), 2-[bis(2-chloroethyl)amino]ethyl ester treated cultures:

| β-alanine, N-(acridin-9-yl), 2-[bis(2-chloroethyl)amino]ethy 1 ester concentration | Vero Cells | T/G/HA-VSMC |
|---|---|---|
| 3 mM | — | na |
| 1 mM | — | — |
| 33 μM | — | — |
| 111 μM | — | — |
| 37 μM | −/+ | - |
| 12 μM | +/− | — |
| 4.1 μM | 1+ | −/+ |
| 1.3 μM | 1+ | 1+ |
| 457 nM | 1+ | 1+ |
| 152 nM | 2+ | 2+ |
| 50 nM | 3+ | 2+ |
| 17 nM | 3+ | 3+ |
| 5.6 nM | 3+ | 3+ |
| 1.9 nM | 3+ | 3+ |
| 600 pM | 4+ | 4+ |
| 200 pM | 4+ | 4+ |
| 70 pM | 4+ | 4+ |
| 23 pM | 4+ | na |

| Score | Effect of treatment |
|---|---|
| — | Lethal treatment, no cells left viable, all rounded, shriveled and dead. |
| −/+ | Some treated cells remain viable, about equal amount of clearly dead cells. |
| +/− | Most cells remain viable, detectable number of dead cells |
| 1+ | All cells appear viable, same density as when treated. |
| 2+ | Minimal proliferation, compared to control. |
| 3+ | Moderate proliferation compared to control. |
| 4+ | Maximal growth, unaffected by treatment. |

The results demonstrate that β-alanine, N-(acridin-9-yl), 2-[bis(2-chloroethyl)amino]ethyl ester inhibited the increase in the number of cultured Human Aortic Smooth Muscle Cells and Vero cells in a dose-dependent manner. Both cell types were rendered incapable of a proliferative response by about the same range of β-alanine, N-(acridin-9-yl), 2-[bis (2-chloroethyl)amino]ethyl ester.

Example 2

Kinetics of inhibition of cultured Human Aortic Smooth Muscle Cells

In this example, proliferation of Humnan Aortic Smooth Muscle Cells as a function of both concentration of reactive agent and time of reaction was investigated. Various compounds were tested to demonstrate the advantages of mustard compounds which target nucleic acids. In addition to the nucleic acidtargeted compounds β-alanine, N-(acridin-9-yl), 2-[b,is(2-chloroethyl)amino]ethyl ester and quinacrine mustard (QM), tile non-nucleic acid targeted compounds chlorambucil, busulfan, melphalan, and mechloretaine were also tested. The structures of these compounds are shown below.

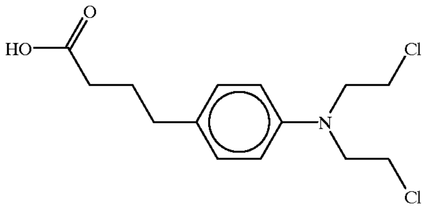

chlorambucil

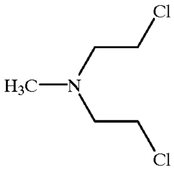

mechlorethamine

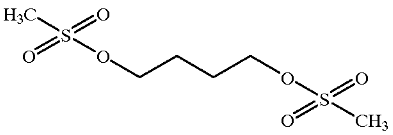

busulfan

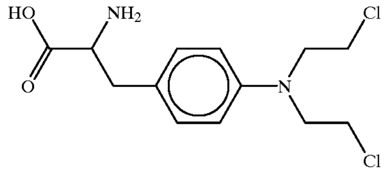

melphalan

T/G Human Aortic Smooth Muscle Cells (obtained from the ATCC, American Type Culture Collection) were used at passage 19, and grown to approximately 60% confluence. The culture medium was F-12K medium with ITS-A reagent (insulin, transferrin and selenium supplement for adherent cell lines), TES and HEPES buffers, ECGS (endothelial cell growth supplement), freshly prepared ascorbate, glutamine, penicillin-streptomycin, and 10% FBS (Gemini) (all other reagents, Life Technologies, or Cellgro). Cells were cultured in 96-well plates.

Ten-fold serial dilutions of P-alanine, N-(acridin-9-yl), 2-[bis(2-chloroethyl)amino]ethyl ester and QM were made in unbuffered saline solution (BBS, blood bank saline) to generate concentrations from 100 μM to 1 nM. Similarly, serial dilutions of chlorambucil, busulfan, melphalan, and mechlorethamine were prepared to generate concentrations of from 1 mM to 10 nM. The stocks were dissolved and diluted immediately prior to use to avoid the possibility of compound degradation.

The growth medium was removed from the smooth muscle cell (SMC)-containing plates. The cell monolayer was then washed with BBS to remove all medium constituents which may quench activity of the compound. The BBS was removed from all wells and 100 μL of each dilution of compound was added to one well each of the tissue culture plates.

Incubation of SMC in the presence of compound was conducted for 15, 30, 60, 90 and 180 seconds. At the conclusion of the incubation, Phosphate Buffered Saline at pH 7.2 (PBS; Life Technologies) was added to each well and immediately removed by aspiration, followed by subsequent washing with PBS to ensure complete removal of each compound solution. This was followed by the addition of growth medium containing 10% FBS for growth promotion, to allow proliferation of cells insufficiently affected by the treatment. Treated cells were then incubated in a 37° C. humidified 5% $CO_2$ incubator (Forma Scientific, Marietta Ohio.).

Growth of cell monolayers was scored eight days following treatment, when a differential growth rate could be determined, using an inverted microscope. Growth was scored subjectively by the careful evaluation of each treated culture and was aided by trypan blue dye exclusion, as follows. Growth medium was removed by aspiration, then 150 μL of a 1:4 dilution of trypan blue diluted in PBS was added to each well for approximately 15 minutes. This was then removed and 250 μL PBS added to each well. Scores assigned to each culture were as defined in Example 1.

Results:

| β-alanine, N-(acridin-9-yl), 2-[bis(2-chloroethyl)amino]ethyl ester | | | | | | |
|---|---|---|---|---|---|---|
| | Time: seconds | | | | | |
| concentration | 0 | 15 | 30 | 60 | 90 | 180 |
| 100 μM | 4+ | — | — | — | — | — |
| 10 μM | 4+ | −/+ | −/+ | −/+ | −/+ | −/+ |
| 1 μM | 4+ | 1+ | 1+ | 1+ | 1+ | +/− |
| 100 nM | 4+ | 1+ | 1+ | 1+ | 1+ | 1+ |
| 10 nM | 4+ | 3+ | 3+ | 3+ | 3+ | 3+ |
| 1 nM | 4+ | 4+ | 4+ | 4+ | 4+ | 4+ |
| 0 | 4+ | 4+ | 4+ | 4+ | 4+ | 4+ |
| Quinacrine Mustard | | | | | | |
| 100 μM | 4+ | — | — | — | — | — |
| 10 μM | 4+ | 1+ | +/− | +/− | +/− | −/+ |
| 1 μM | 4+ | 2+ | 2+ | 2+ | 2+ | 1+ |
| 100 nM | 4+ | 3+ | 3+ | 3+ | 2+ | 2+ |
| 10 nM | 4+ | 4+ | 4+ | 4+ | 4+ | 4+ |
| 1 nM | 4+ | 4+ | 4+ | 4+ | 4+ | 4+ |
| 0 | 4+ | 4+ | 4+ | 4+ | 4+ | 4+ |
| Chlorambucil | | | | | | |
| 1 mM | 4+ | — | — | — | — | — |
| 100 μM | 4+ | +/− | +/− | +/− | +/− | −/+ |
| 10 μM | 4+ | 1+/2+ | 1+/2+ | 1+ | 1+ | +/− |
| 1 μM | 4+ | 4+ | 4+ | 4+ | 4+ | 3+ |
| 100 nM | 4+ | 4+ | 4+ | 4+ | 4+ | 4+ |
| 10 nM | 4+ | 4+ | 4+ | 4+ | 4+ | 4+ |
| 0 | 4+ | 4+ | 4+ | 4+ | 4+ | 4+ |
| Busulfan | | | | | | |
| 1 mM | 4+ | 4+ | 4+ | 4+ | 4+ | 4+ |
| 100 μM | 4+ | 4+ | 4+ | 4+ | 4+ | 4+ |
| 10 μM | 4+ | 4+ | 4+ | 4+ | 4+ | 4+ |
| 1 μM | 4+ | 4+ | 4+ | 4+ | 4+ | 4+ |
| 100 nM | 4+ | 4+ | 4+ | 4+ | 4+ | 4+ |
| 10 nM | 4+ | 4+ | 4+ | 4+ | 4+ | 4+ |
| 0 | 4+ | 4+ | 4+ | 4+ | 4+ | 4+ |

-continued

| β-alanine, N-(acridin-9-yl), 2-[bis(2-chloroethyl)amino]ethyl ester | | | | | | |
|---|---|---|---|---|---|---|
| | Time: seconds | | | | | |
| concentration | 0 | 15 | 30 | 60 | 90 | 180 |
| Melphalan | | | | | | |
| 1 mM | 4+ | 2+ | 2+ | 2+ | 2+ | 1+ |
| 100 μM | 4+ | 3+ | 3+ | 3+ | 3+ | 3+ |
| 10 μM | 4+ | 4+ | 4+ | 4+ | 4+ | 4+ |
| 1 μM | 4+ | 4+ | 4+ | 4+ | 4+ | 4+ |
| 100 nM | 4+ | 4+ | 4+ | 4+ | 4+ | 4+ |
| 10 nM | 4+ | 4+ | 4+ | 4+ | 4+ | 4+ |
| 0 | 4+ | 4+ | 4+ | 4+ | 4+ | 4+ |
| Mechlorethamine | | | | | | |
| 1 mM | 4+ | 2+ | 2+ | 1+ | 1+ | 1+ |
| 100 μM | 4+ | 3+/4+ | 3+ | 3+ | 3+ | 2+ |
| 10 μM | 4+ | 4+ | 4+ | 4+ | 3+ | 3+ |
| 1 μM | 4+ | 4+ | 4+ | 4+ | 4+ | 4+ |
| 100 nM | 4+ | 4+ | 4+ | 4+ | 4+ | 4+ |
| 10 nM | 4+ | 4+ | 4+ | 4+ | 4+ | 4+ |
| 0 | 4+ | 4+ | 4+ | 4+ | 4+ | 4+ |

These results indicate that β-alanine, N-(acridin-9-yl), 2-[bis(2-5 chloroethyl)amino]ethyl ester inhibited the increase in the number of cultured Human Aortic Smooth Muscle Cells in a dose-dependent manner with a relatively broad therapeutic window. The results of this study are consistent with a 15 second treatment, with between approximately 1 μM to 100 nM β-alanine, N-(acridin-9-yl), 2-[bis(2-chloroethyl)amino]ethyl ester, being an effective means of preventing smooth muscle cell proliferation following balloon angioplasty for occluded coronary arteries. All mustard compounds showed some effect, with those having a nucleic acid targeting group being more effective at lower concentrations and/or shorter exposure times.

Example 3

Evaluation of Concentration Ranges for β-alanine, N-(acridin-9-yl), 2-[bis(2-chloroethyl)amino]ethyl ester.

The following experiment identifies the range of concentrations of β-alanine, N-(acridin-9-yl), 2-[bis(2-chloroethyl) amino]ethyl ester that causes cytostasis in human aortic smooth muscle cells (SMCs).

Human aortic SMCs at low passage are seeded into a 12 well tissue culture plate at a density of 10,000 cells per $cm^2$ in 10% fetal bovine serum and 90% F12K medium with 2 mnM glutamine, 10 mM HEPES, 10 mM TES, 50 μM ascorbic acid, 10 μg/ml insulin, 5.5 μg/ml transferrin, 6.7 ng/ml sodium selenite and 30 μg/ml endothelial cell growth supplement. After 18 hours of attachment, the medium is removed and 2 ml of phosphate buffered saline is added to wash growth medium from the monolayer. The PBS is then removed and replaced by 1.5 ml/well of an identically formulated F12K medium that lacks FBS, to induce the cells to enter the resting $G_o$ state. This treatment synchronizes the cells so that this test will accurately assess the ability of β-alanine, N-(acridin-9-yl), 2-[bis(2-chloroethyl)amino] ethyl ester to arrest growth cycle progression.

After 48–72 hours of synchronization, the SMCs are treated with β-alanine, N-(acridin-9-yl), 2-[bis(2-chloroethyl)amino]ethyl ester over a concentration range of 300 nM to 1 μM. A minimum of 30 minutes is allowed for the equilibration of drug. A negative control for 10% fetal bovine serum and an untreated fetal bovine serum stimulated control is included.

Following incubation, the medium is removed and replaced by medium containing 10% fetal bovine serum to allow the proliferation of cells unaffected by the treatment. Cultures are then incubated at 37° C. with growth medium changes every 2–3 days to sustain cell growth.

Analysis of Cell Count following Treatment of Human Aortic Smooth Muscle Cells.

Cell count for each sample, taken by direct counting with a hemacytometer, is measured at several time points over a 28 day period. At every time point and media replacement, a 1 ml aliquot of each sample is removed and preserved at −80° C. for cytokine studies described below. The remaining recovered cells are preserved at −80° C for subsequent analysis of nuclear DNA content by flow cytometry.

Analysis of Cell Cycle following Treatment of Human Aortic Smooth Muscle Cells.

Measurements of SMCs cell cycle are performed by flow cytometric analysis of nuclear DNA content in cryopreserved samples according to an established protocol for the Becton-Dickinson FACScan, as further detailed in the literature with specific reference to SMCs. See, e.g. March et al., *Circulation* 87, 184–191 (1993).

Measurement of Cytokine Production in Treated Human Aortic Smooth Muscle Cells.

Samples are examined for their production of various cytokines that are connected with cell proliferation and response to injury. The screen consists of performing ELISA immunoassays using commercially available assays for the detection of human cytokines, including interleukin 1 β (IL-1β), interleukin 8, vascular endothelial growth factor (VEGF), platelet-derived growth factor (PDGF) and endothelin-1.

While the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

What is claimed is:

1. A method for inhibiting restenosis, the method comprising local administration of an alkylating compound to a site of vascular recanalization, wherein said alkylating

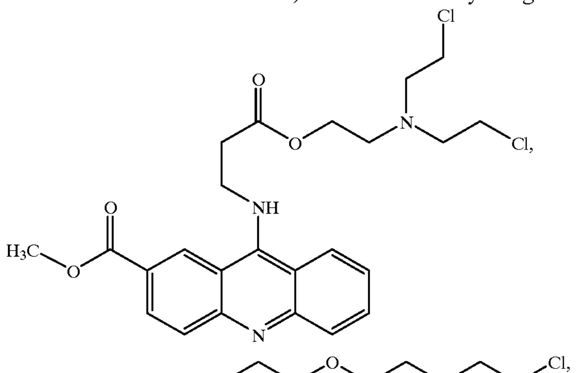

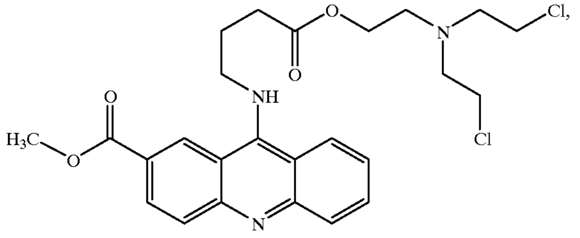

-continued

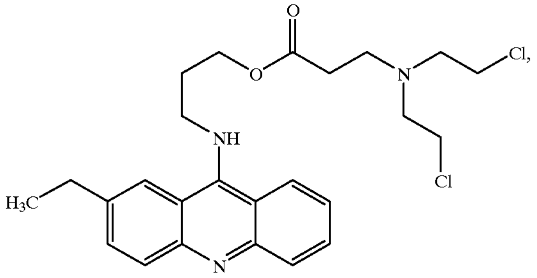

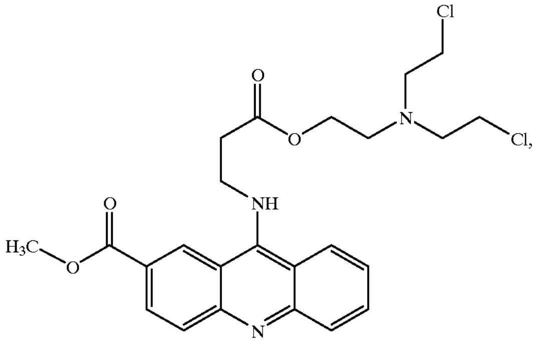

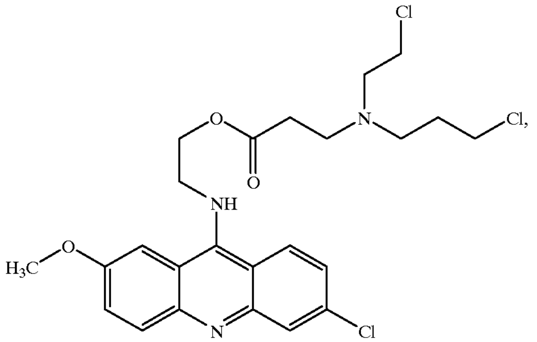

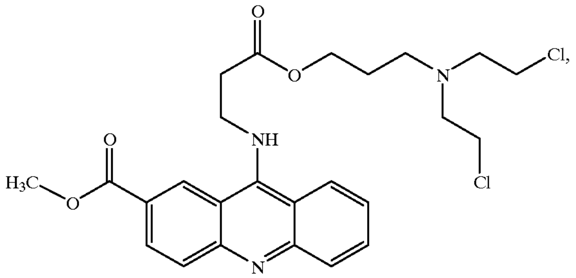

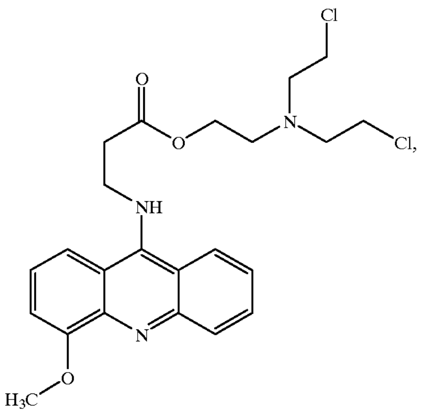

-continued

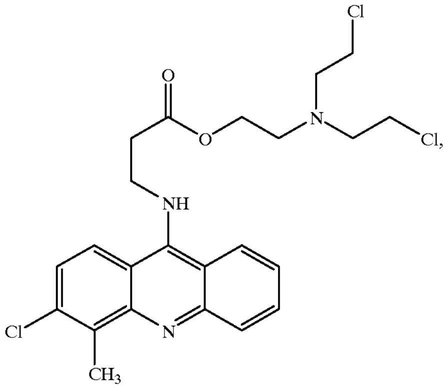

,

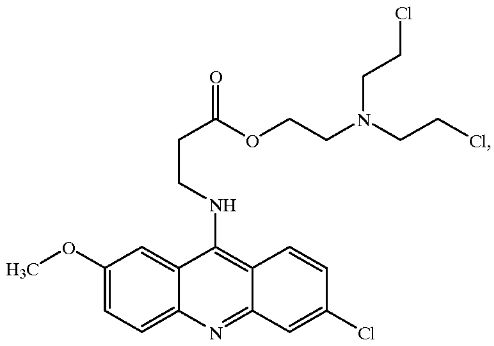

,

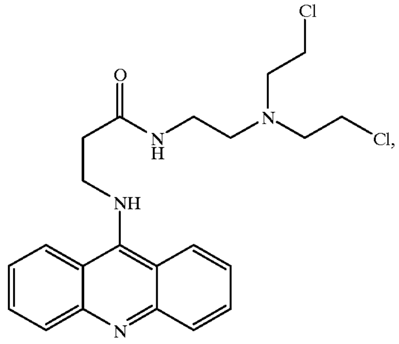

,

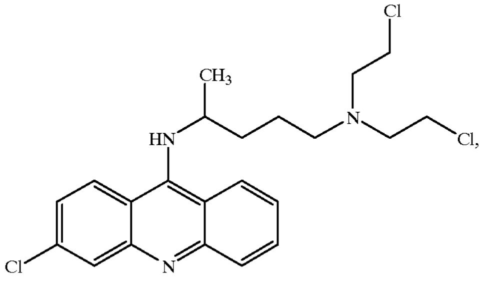

, and

-continued

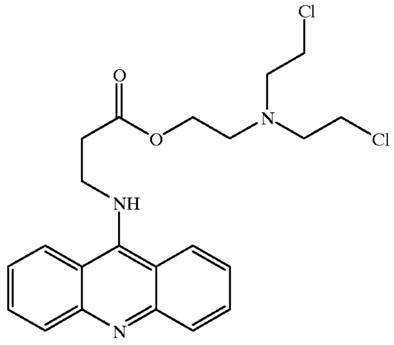

compound is selected from the group consisting of: and all salts thereof.

2. The method according to claim 1, wherein administration is achieved through the use of a system selected from the group consisting of catheters, stents and endoluminal paving.

3. The method according to claim 2, wherein administration is achieved through the use of an intravascular drug delivery catheter.

4. The method according to claim 3, wherein said catheter is selected from the group consisting of an infusion sleeve catheter, a pressure-driven catheter and a double balloon catheter.

5. The method according to claim 1, wherein the method further comprises administration of a quencher.

6. The method according to claim 5, wherein the quencher is administered locally.

7. The method according to claim 5, wherein the quencher is administered systemically.

8. The method according to claim 5, wherein the quencher is a thiol-containing molecule.

9. The method according to claim 8, wherein the quencher is glutathione.

10. The method according to claim 1, wherein the vascular recanalization is achieved by balloon angioplasty.

11. The method according to claim 1, wherein the local administration of an alkylating compound is of a non sustained release formulation.

* * * * *